United States Patent [19]

Chang

[11] Patent Number: 4,486,341
[45] Date of Patent: Dec. 4, 1984

[54] FRACTIONATION OF BLOOD PLASMA

[75] Inventor: Chong E. Chang, La Canada, Calif.

[73] Assignee: Alpha Therapeutic Corporation, Los Angeles, Calif.

[21] Appl. No.: 393,030

[22] Filed: Jun. 28, 1982

[51] Int. Cl.$^3$ .............................................. C07G 7/00
[52] U.S. Cl. .......................... 260/112 B; 260/112 R; 260/118; 260/120; 260/122; 424/101
[58] Field of Search ............... 260/112 B, 112 R, 122, 260/120, 118; 210/957, 805; 424/101

[56] References Cited

U.S. PATENT DOCUMENTS

| | | | |
|---|---|---|---|
| 2,390,074 | 12/1945 | Cohn | 260/122 |
| 3,764,009 | 10/1973 | Watt | 210/96 |
| 4,066,549 | 1/1978 | Oeser et al. | 260/112 B |
| 4,067,863 | 1/1978 | Watt et al. | 260/112 B |
| 4,379,083 | 4/1983 | Falke et al. | 260/112 B |

OTHER PUBLICATIONS

E. J. Cohn et al., *Preparation and Properties of Serum and Plasma Proteins, IV, A System for the Separation into Fractions of the Protein and Lipoprotein Components of Biological Tissues and Fluids,* The Journal of the American Chemical Society, vol. LXVIII (Jan.–Jul. 1946), pp. 459–475.

*Primary Examiner*—John Kight
*Assistant Examiner*—Garnette D. Draper
*Attorney, Agent, or Firm*—Christie, Parker & Hale

[57] ABSTRACT

There is provided in accordance with practice of this invention a process for separating protein fractions from a solution containing proteins and an apparatus for practicing the process. The process and apparatus involve withdrawing from a suspension tank a portion of the suspension contained therein to form a recycle stream. The withdrawn suspension forming the recycle stream contains particles of a selected protein fraction precipitated from a solution containing proteins. Fresh protein solution comprising proteins of the selected protein fraction is mixed into the recycle stream to form a mixed recycle stream. At least a portion of the selected protein fraction proteins in the fresh protein solution precipitate onto previously precipitated selected protein fraction particles suspended in the mixed recycle stream. The mixed recycle stream is introduced back into the suspension tank. A portion of the suspension is withdrawn from the suspension tank in a product stream and precipitated, selected protein fraction particles are recovered from the product stream.

32 Claims, 2 Drawing Figures

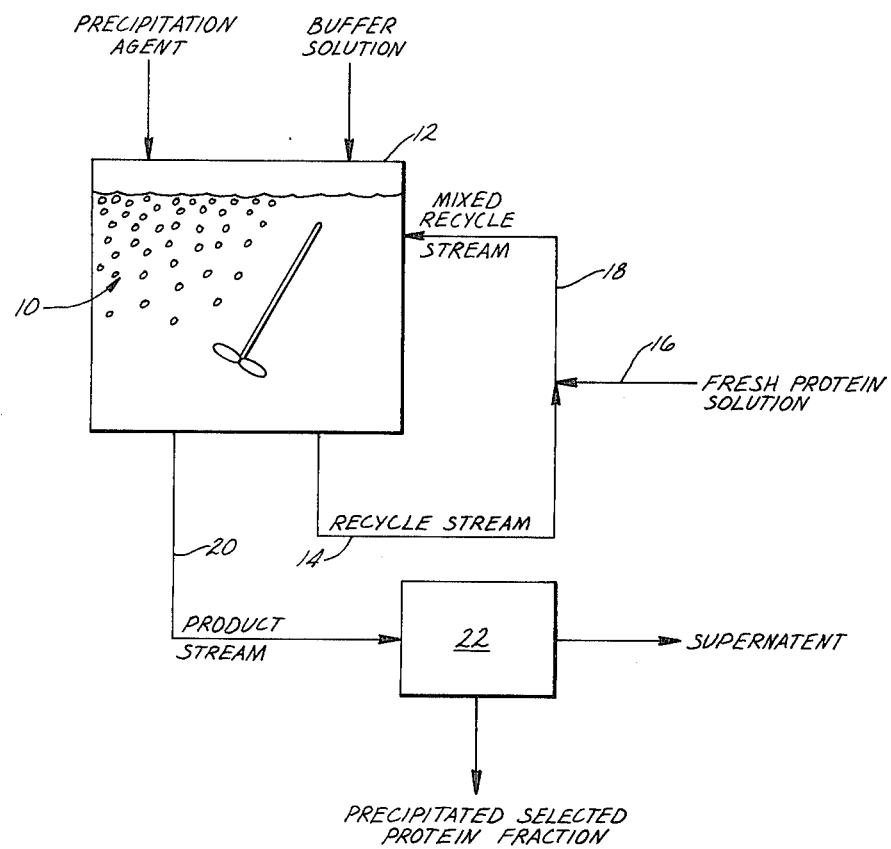

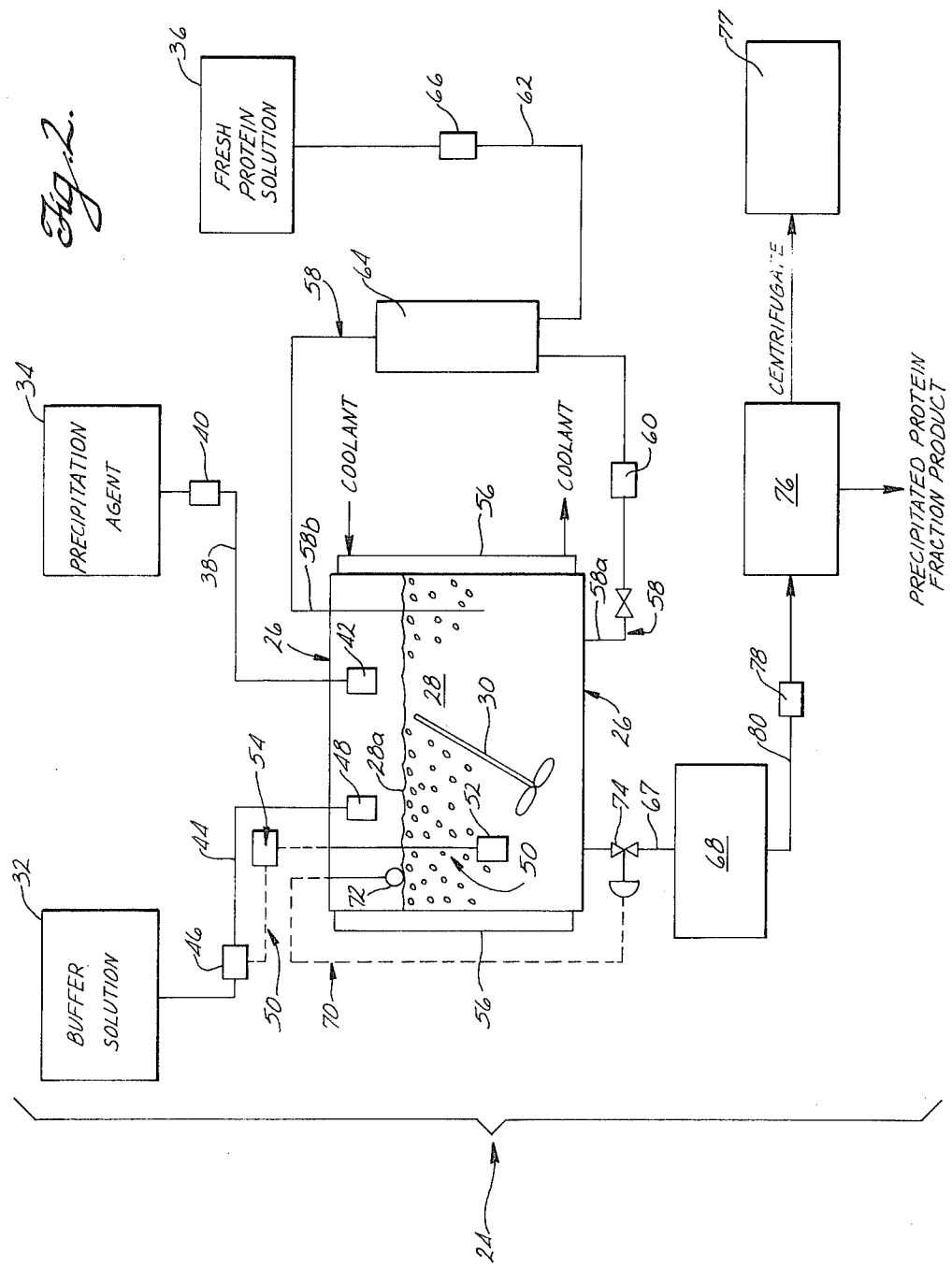

FRACTIONATION OF BLOOD PLASMA

FIELD OF THE INVENTION

The process and apparatus provided in accordance with practice of this invention are useful for continuously separating protein fractions from solutions containing proteins.

BACKGROUND OF THE INVENTION

Human blood is made up of approximately 35 percent cellular components, including red cells, white cells, and platelets with the remaining 65 percent being a fluid called plasma. The plasma suspends the cells and platelets and comprises a solution of approximately 90 percent water, 7 percent protein, and 3 percent various other organic and inorganic solutes.

The protein portion of plasma consists of various different protein fractions including, for example, albumin, fibrinogen, gamma ($\gamma$) globulin, alpha ($\alpha$) and beta ($\beta$) globulins, and others.

For various human therapies, it can be desired to separate and concentrate blood protein fractions so that only a selected single fraction is administered to a patient. For example, it can be particularly desirable to separate albumin from the plasma and provide the separated albumin in a concentrated solution for patient therapy.

Methods for separating protein fractions from plasma are disclosed in U.S. Pat. No. 2,390,074 to E. J. Cohn and in E. J. Cohn, L. E. Strong, W. L. Hughes, D. J. Mulford, J. N. Ashworth, M. Melin and H. L. Taylor, *Separation Into Fractions of Protein and Lipoprotein Components*, J. Am. Chem. Soc. 68 (1946), p 459–475. Both U.S. Pat. No. 2,390,074 and the American Chemical Society article are incorporated herein by this reference. The protein fractions are separately precipitated by adding a precipitating agent or precipitant such as ethanol to the plasma and maintaining the plasma solution at a desired pH, temperature, ethanol concentration, and ionic strength to precipitate the desired fraction.

The Cohn process is essentially a batch process where the various proteins are precipitated from the solution sequentially. The proteins are grouped into fractions with as much as possible of the fibrinogen in the plasma precipitated first as Fraction I. Next, Fractions II and III which are designated the $\gamma$ globulin fractions are precipitated together. Fraction IV-1, rich in lipid and $\alpha$-globulins, is then precipitated, followed by precipitation of remaining $\alpha$-globulins in combination with $\beta$-globulins as Fraction IV-4. Albumin remaining in the supernatant (centrifugate) is next precipitated as Fraction V to obtain a concentrated albumin fraction.

In each case, after the desired fraction is precipitated, the conditions of the supernatant plasma are changed to precipitate the next fraction.

During the time interval required to adjust the supernatant to its equilibrium condition for the next precipitation, protein fractions that desirably remain in solution can precipitate. For example, when the supernatant is being adjusted to conditions for precipitating an earlier fraction, albumin can precipitate, thus contaminating the earlier fraction and also reducing the amount of albumin that can finally be recovered. Additionally, batch processes can be slower than desired.

Thus, there is a need in the art for a simple and efficient process for precipitating protein fractions continuously that maximizes the amount of protein of a desired purity recovered.

SUMMARY OF THE INVENTION

There is, therefore, provided in practice of this invention a process for continuous separation of protein fractions from a solution containing proteins and an apparatus for practicing the process. A suspension that contains a precipitation agent and precipitated particles of a selected protein fraction is in a suspension tank. The suspension is maintained at a selected pH, temperature, and precipitation agent concentration for selectively precipitating the selected protein fraction. A portion of the suspension is withdrawn from the suspension tank to form a recycle stream. A protein solution comprising proteins of the selected protein fraction is continuously mixed into the recycle stream to thereby form a mixed recycle stream. At least a portion of the selected protein fraction proteins in the protein solution precipitate onto previously precipitated selected protein fraction particles suspended in the mixed recycle stream. The mixed recycle stream is introduced back into the suspension tank. A portion of the suspension is also continuously withdrawn from the suspension tank in a product stream. Precipitated selected protein fraction particles are recovered from the product stream.

BRIEF DESCRIPTION OF THE DRAWINGS

These and other features, aspects, and advantages of the present invention will become more apparent when considered with respect to the following description, appended claims, and accompanying drawings wherein:

FIG. 1 is a schematic diagram showing principles of practice of the process of this invention for separating protein fractions from solutions containing proteins; and FIG. 2 is a schematic view of one embodiment of an apparatus provided for separating protein fractions from a solution containing proteins according to practice of the process of this invention.

DETAILED DESCRIPTION

Referring to FIG. 1, a generalized schematic diagram is provided showing principles of the process of this invention for recovering a selected protein fraction from a solution containing proteins.

A suspension 10 containing particles of a selected protein fraction precipitated from a solution comprising proteins is mixed at a selected temperature in a tank 12 with a precipitation agent and a buffer solution. The amount of buffer and precipitation agent in the suspension provide the suspension with a pH and precipitation agent concentration so that, at the selected temperature, only the selected protein fraction precipitates. Thus, other proteins that are present remain in solution.

A portion of the suspension is withdrawn from the tank in a recycle stream 14. Fresh protein solution that includes proteins of the selected protein fraction is introduced in stream 16 into the recycle stream 14 forming a mixed recycle stream 18. At least a portion of the selected protein fraction in the fresh protein solution precipitates onto previously precipitated selected protein fraction particles in the mixed recycle stream. The mixed recycle stream is introduced back into the suspension in the tank 12.

A portion of the suspension is withdrawn from the tank 12 in a product stream 20. The product stream is sent to a separation means 22 where the precipitated selected protein fraction particles are separated from a supernatant and recovered.

If desired, the above described process can be provided in a plurality of stages in series with the supernatant from a preceding stage being sent to the next stage for recovery of a selected protein fraction remaining in the supernatant. In such a system, the process can be repeated from stage to stage at different combined conditions of pH, temperature, and precipitation agent concentration as desired until all of the desired protein fractions are separated.

The basic separation chemistry used in practice of this invention is that developed by Cohn and described in E. J. Cohn et al, *Separation Into Fractions of Protein and Lipoprotein Components,* J. Am. Chem. Soc. 68 (1946), p 459–475. This article is incorporated hereinabove by reference.

Referring to FIG. 2, there is shown a schematic view of a preferred embodiment of an apparatus 24 provided for separating protein fractions from a solution containing proteins according to practice of the process described above.

A tank 26 is provided for holding a suspension 28 containing particles of a selected protein fraction precipitated from a protein containing solution. The precipitated particles are maintained in suspension by an agitator 30 in the tank.

Separate supply containers 32, 34, and 36, respectively, are provided for a buffer solution, a liquid precipitation agent or precipitant, and fresh protein containing solution.

Precipitation agents useful in practice of principles of this invention are alcohols, acetone, and other water miscible organic solvents. Ethanol is the preferred precipitation agent and, for purposes of exposition herein, the process is described below using ethanol. Other precipitation agents can be used if desired.

A pipeline 38 connects the ethanol or precipitant tank 34 to the top of the suspension tank 26. A metering pump 40 in the line 38 pumps the ethanol from the tank 34 into the top of the suspension tank 26. Preferably, a spray nozzle 42 is on the end of the line 38 for disbursing the ethanol in a fine mist as it enters the suspension tank.

As is described below in greater detail, the level of the suspension in the tank 26 is maintained below the top of the tank. Preferably, the spray nozzle 42 is located above the top surface 28a of the suspension in the tank so that the ethanol is sprayed onto the surface of the suspension. Spraying the precipitant onto the surface of the suspension tends to eliminate foaming, which has been found to denature the proteins being recovered.

If desired, more than one spray nozzle can be provided for spraying the ethanol uniformly across the suspension surface.

The buffer solution tank 32 is connected to the top of the suspension tank 26 by a pipeline 44. A metering pump 46 in the line 44 pumps the buffer solution from the tank 32 into the top of the tank. As was the case with ethanol, preferably a spray nozzle 48 is on the end of the line 44 for disbursing the buffer solution in a fine mist as it enters the tank. The spray nozzle 48 preferably is located above the top surface 28a of the suspension in the tank so that the buffer is sprayed onto the surface of the suspension. As was the case with spraying the ethanol, the buffer spray tends to eliminate foaming. Additionally, more than one nozzle can be provided if desired for spraying the buffer into the tank.

It is preferred that the particle size of both the ethanol droplets and the buffer solution droplets sprayed into the tank are as small as possible so that the time it takes to mix the ethanol and buffer into the suspension is minimized. It has been found that when mixing time is reduced, precipitation of proteins from fractions other than the selected fraction is inhibited. Thus, by providing the buffer and ethanol in small droplets to reduce mixing time, unwanted precipitation is reduced which, in turn, enhances the purity of the product and increases yields.

In one exemplary embodiment of the apparatus 24, the ethanol spray nozzle 42 and the buffer spray nozzle 48 provide an average ethanol and buffer particle size of between about 50 and 100 microns ($\mu$m). Having an average particle size between 50 and 100 $\mu$believed to result in mixing that is rapid enough to substantially eliminate precipitation of unwanted fractions. Thus, although spray nozzles providing any size droplets can be used, those that provide an average droplet size of less than about 100 $\mu$m are preferred.

Additionally, it has been found that adding ethanol to a protein suspension can create localized overheating which can tend to denature the proteins. Spraying the alcohol into the tank in a fine mist reduces such overheating and thus reduces the occurrence of protein denaturation.

As is mentioned above, the selected protein fraction is precipitated by maintaining the suspension 28 at a pH, ethanol concentration, and temperature so that proteins of the selected fraction are precipitated, while other protein fractions remain in solution.

The pH of the suspension is controlled by an automatic pH control and monitoring system generally shown at 50. In the illustrated embodiment, the pH system comprises a pH probe 52 in the tank operatively connected via a pH controller 54 to the buffer solution metering pump 46. In operation, the desired pH for precipitation of the selected protein fraction is set on the controller. The metering pump 46 is automatically controlled to pump more or less buffer solution from the buffer solution tank 32 into the suspension tank 26 to maintain the desired pH.

Depending on the pH value desired for precipitating a particular protein fraction, the buffer solution can be acidic or basic. Buffers useful in practice of this invention are described below in greater detail.

The temperature of the suspension in the tank 12 is monitored and controlled by an automatic temperature control and monitoring system (not shown). Since the precipitation reaction is exothermic, the suspension must be cooled to maintain its temperature within the desired range. Preferably, a cooling jacket 56 is provided on the tank 26 through which a coolant flows. The automatic temperature monitoring and control system maintains proper coolant conditions so that the suspension temperature is automatically maintained at its desired value.

Systems useful for both automatic pH and temperature control are commercially available.

A recycle line 58 is connected at its inlet end 58a to the suspension tank for withdrawing the suspension from the tank and is connected at its outlet end 58b to the suspension tank for recycling the suspension back into the tank. Preferably, the recycled suspension is introduced back into the suspension in the tank below its surface 28a to reduce foaming. A recycle pump 60 is in the line 58 between the inlet and outlet to recycle the suspension.

Fresh protein solution is added to the system from the protein supply tank 36. A supply line 62 connects the protein tank 36 to the recycle line 58 either at or just upstream of a static mixer 64 in the recycle line. A protein solution pump 66 pumps the fresh protein solution from the tank 36 into the recycle stream in the line 58 so that the fresh protein is mixed with the recycling suspension in the mixer 64. This forms a mixed recycle stream downstream of the mixer in that portion of the recycle line between the mixer and the tank 26. The mixed recycle stream is returned to the tank.

Preferably, the fresh protein solution is pumped continuously into the system to provide a continuous protein separation process.

As is mentioned above, the suspension withdrawn from the suspension tank to form the recycle stream is at the proper conditions of pH, ethanol concentration, and temperature for precipitating the selected protein fraction from solution. Thus, proteins of the selected fraction contained in the fresh protein solution precipitate on previously precipitated selected protein fraction particles in the suspension as it passes through the recycle line.

It is thought that precipitation of the selected protein fraction from the fresh protein solution is virtually complete by the time the mixed recycle stream re-enters the tank 26. Since the selected protein fraction tends to precipitate in the recycle line on previously precipitated particles, the average particle size of the precipitate is increased. This enhances the ease of separation of the precipitate from the suspension and tends to increase yields from the process.

Additionally, the entering fresh protein solution does not encounter a wide range of pH and temperature conditions as is the case in a batch process, as the batch is being brought to equilibrium conditions for precipitation. Thus, proteins are less likely to be denatured by practice of this invention.

The ethanol concentration in the suspension required to precipitate the selected protein fraction is maintained by adjusting the flow rate of ethanol into the tank 26, based on the amount of fresh protein solution being introduced.

Precipitated particles of the selected protein fraction are recovered by removing the suspension from the tank and sending it to a separator such as a centrifuge.

In an exemplary embodiment, the suspension is removed from the suspension tank 26 in a product stream which flows through a pipeline 67 into a product receiving tank 68.

The amount of suspension removed from the tank as product is balanced against the amount of material entering the system to maintain the tank at a constant level. The desired level is automatically maintained by a level control system generally shown at 70. The level control system 70 comprises a float 72 operatively connected to an outlet valve 74 in the line 67 between the suspension tank and the product tank 68. The valve 74 is throttled open or closed by a signal from the level control system to maintain the desired suspension tank level.

The suspension is pumped from the product receiving tank 68 into a centrifuge 76 by a pump 78. The pump is in a line 80 that connects the product tank to the centrifuge. If desired, the product receiving tank can be eliminated and the suspension can be sent directly to the centrifuge from the suspension tank.

The precipitated selected protein fraction particles are separated in the centrifuge from the suspension forming a supernatant or centrifugate and a paste comprising the selected protein fraction particles. The selected protein fraction particles and the centrifugate are then recovered.

If desired, after a first protein fraction is recovered from a protein solution using the apparatus 24, the same apparatus can be used for recovery of another protein fraction from the centrifugate recovered from the first separation. This process can be repeated until all desired protein fractions are separated.

Alternatively and preferably, a plurality of apparatus such as the apparatus 24 can be provided in series operation. In such a system, each apparatus 24 provides one stage or module for separating a particular protein fraction from a protein solution For example, the centrifugate from a previous stage can be collected in a centrifugate container 77 and the centrifugate can be introduced as fresh protein solution into the next stage. Any number of stages can be used depending upon the number of protein fractions being separated.

An example of use of the apparatus 24 for sequentially separating a plurality of selected protein fractions from the protein containing solution blood plasma in accordance with this invention is set forth below.

EXAMPLE 1

Separating Protein Fraction I From Blood Plasma

Using an apparatus similar to the apparatus 24 described above, protein fraction I was precipitated from blood plasma and recovered.

A buffer solution comprising 0.1 molar acetic acid and 8 percent by volume ethanol was prepared and poured into the buffer solution tank 32. A precipitant (precipitation agent) solution comprising 53.3 percent by volume ethanol and water was prepared and poured into the ethanol tank 34. Fresh blood plasma having a pH of about 7.99 was prepared and poured into the fresh protein solution or plasma tank 36.

To start the process, the buffer pump 46, recycle pump 60, precipitant pump 40, and protein solution pump 66 were all started simultaneously to introduce the respective fluids into the suspension tank 26. The pump settings were as follows: the protein pump was set at 1,000 milliliters (ml) per minute; the precipitant pump was set at 174 ml per minute; the buffer pump was set at 71 ml per minute; and the recycle pump was set at 10 liters (l) per minute.

The suspension being formed in the tank 26 was thoroughly mixed by the agitator or impeller 30 which was turning at 100 revolutions per minute and was cooled to about $-2°$ C. by coolant flowing through in the coolant jacket 56 on the tank. The temperature was maintained at $-2°$ C. automatically by setting the automatic temperature monitoring and control system accordingly. The blood plasma in the tank 36, the buffer solution in the tank 32, and the ethanol in the tank 34 was maintained and pumped into the suspension tank at from about $+2°$ C. to about $-5°$ C.

When the pH of the suspension being formed reached about 7.0, the pH controller was set at 7.0 and the pH was thereafter maintained near this value (between 6.85 and 7.14 as measured by laboratory sample) by automatically operating the buffer pump as needed.

During the initial formation of the suspension 28 in the tank, fraction I proteins precipitated from solution. Although, during startup other protein fractions may also have precipitated, they are redissolved in solution once equilibrium conditions for the fraction I precipitate are met.

Example 3, protein fraction IV-1 was separated from the centrifugate prepared in Example 2. In Example 4, fraction IV-4 was separated from the centrifugate prepared in Example 3 and, in Example 5, protein fraction V was separated from the centrifugate prepared in Example 4.

The operating conditions for Examples 1 through 5 are summarized in Table I as follows:

TABLE I

OPERATING CONDITIONS FOR EXAMPLES 1-5

| Example No. | Retention Time in Suspension Tank | Protein Fraction Recovered | Ethanol Concentration in Suspension (% by vol.) | pH Range in Suspension | Temperature of Suspension | Buffer Solution Used |
|---|---|---|---|---|---|---|
| 1 | 24 min. | I | 8 | 6.85–7.14 | −2° C. | .1 M acetic acid in 8% ethanol |
| 2 | 20 min. | II & III | 20 | 6.85–6.95 | −5° C. | .1 M acetic acid in 20% ethanol |
| 3 | 19 min. | $IV_1$ | 20 | 5.24–5.26 | −5° C. | .3 M acetic acid in 20% ethanol |
| 4 | 14 min. | $IV_4$ | 40 | 5.91–5.93 | −5° C. | .2 M sodium bicarbonate in 40% ethanol |
| 5 | 13 min. | V | 40 | 4.81–4.83 | −6° C. | .8 M acetic acid in 40% ethanol |

| Example No. | Protein Solution Flow Rate (l/min.) | Ethanol Solution Concentration in Ethanol Tank (% by vol.) | Suspension Recycle Rate (l/min.) | Ethanol Flow Rate (ml/min.) | Buffer Solution Flow Rate (ml/min. average) |
|---|---|---|---|---|---|
| 1 | 1.000 | 53.3 | 10 | 174 | 71 |
| 2 | 1.207 | 95.0 | 10 | 186 | 77 |
| 3 | 1.396 | — | 10 | No ethanol added | 189 |
| 4 | 1.486 | 95.0 | 10 | 568 | 178 |
| 5 | 2.062 | — | 10 | No ethanol added | 182 |

The conditions of the suspension desired for selectively precipitating fraction I are a pH of about 7.0, temperature of about −2° C. and an ethanol concentration of about 8 percent by volume.

The level of suspension desired to be maintained in the suspension tank 26 was set at about 30 liters. At 30 liters, the top of the suspension was below the top of the tank so that the buffer solution and ethanol could be sprayed into the tank as described above. The level was controlled automatically by the liquid level controller 70. Thus, when the level reached 30 liters, the discharge valve 74 was throttled open to discharge the suspension continuously at the same rate as the fresh plasma, ethanol, and buffer were being added to the tank. The estimated retention time of the suspension in the tank was 24 minutes.

The suspension was discharged from the suspension tank into the product receiving tank 68 and was then pumped from the receiving tank to the centrifuge 76 for separation. The fraction I precipitate was recovered from the centrifuge and a centrifugate was recovered and held for further processing.

In each of the following examples, one or more selected protein fraction was separated from the centrifugate recovered from a previous separation.

In Example 2, protein fractions II and III were separated from the centrifugate prepared in Example 1. In No ethanol was added to the suspension tank in Examples 3 and 5 because the centrifugate recovered from Examples 2 and 4 and used in Examples 3 and 5, respectively, already had the proper ethanol concentration for precipitation of the desired fractions.

Typical analyses of the selected protein fractions recovered by the exemplary process described above are set forth in Table II.

TABLE II

TYPICAL COMPOSITION OF RECOVERED PROTEIN FRACTIONS (% BY WEIGHT)

| Example No. | Protein Fraction | Serum Albumin | α-Globulin | β-Globulin | γ-Globulin | Fibrinogen |
|---|---|---|---|---|---|---|
| 1 | I | 24.9 | 9.6 | 17.4 | 19.6 | 28.5 |
| 2 | II & III | 11.6 | 15.0 | 12.6 | 49.1 | 11.7 |
| 3 | $IV_1$ | 23.9 | 25.2 | 14.8 | 36.1 | — |
| 4 | $IV_4$ | 34.3 | 32.8 | 32.9 | — | — |
| 5 | V | 92.4 | 3.8 | 3.8 | — | — |

It is estimated that at least about 82% of the original albumin that is introduced into the system in the fresh plasma can be recovered by practice of this invention in Fraction V.

The above description of a preferred embodiment of a process for separating selected protein fractions from a solution containing proteins and apparatus useful for practicing the separations is for illustrative purposes. Because of variations which will be apparent to those skilled in the art, the present invention is not intended to be limited to the particular embodiments described above. The scope of the invention is defined in the following claims.

What is claimed is:

1. A process for recovering a selected protein fraction from a solution containing proteins, the process comprising the steps of:
   providing a suspension containing a precipitation agent and precipitated particles of a selected protein fraction in a suspension tank;
   maintaining the suspension at a selected pH, temperature, and precipitation agent concentration for selectively precipitating the selected protein fraction;
   withdrawing a portion of the suspension from the suspension tank to form a recycle stream;
   mixing a protein solution comprising proteins of the selected protein fraction directly into the recycle stream to thereby form a mixed recycle stream, whereby at least a portion of the selected fraction proteins in the protein solution precipitate onto previously precipitated selected protein fraction particles suspended in the mixed recycle stream;
   introducing the mixed recycle stream back into the suspension tank;
   withdrawing a portion of the suspension from the suspension tank in a product stream; and
   recovering from the product stream the precipitated selected protein fraction particles.

2. The process according to claim 1 comprising maintaining the suspension at the selected pH by spraying a buffer solution into the tank onto the top surface of the suspension in the tank.

3. The process according to claim 1 comprising maintaining the suspension at the selected precipitation agent concentration by spraying the precipitation agent into the tank onto the top surface of the suspension in the tank.

4. The process according to claim 1 wherein the precipitation agent is ethanol.

5. A process for recovering a selected protein fraction from a solution containing proteins, the process comprising the steps of:
   withdrawing from a suspension tank a portion of a suspension contained therein to form a recycle stream, the withdrawn suspension containing particles of a selected protein fraction precipitated from a solution containing proteins;
   mixing fresh protein solution comprising proteins of the selected protein fraction directly into the recycle stream to thereby form a mixed recycle stream, whereby at least a portion of the selected protein fraction proteins in the fresh protein solution precipitate onto previously precipitated selected protein fraction particles suspended in the mixed recycle stream;
   introducing the mixed recycle stream back into the suspension tank;
   withdrawing a portion of the suspension from the suspension tank in a product stream; and
   recovering from the product stream the precipitated selected protein fraction particles.

6. The process according to claim 5 additionally comprising spraying a selected amount of buffer solution and a selected amount of precipitation agent separately onto the surface of the suspension in the suspension tank and mixing the buffer solution and precipitation agent into the suspension so that the suspension is maintained at a pH and precipitation agent concentration sufficient to selectively precipitate the selected protein fraction.

7. The process according to claim 6 wherein the precipitation agent is ethanol.

8. A process for recovering a selected protein fraction from a solution containing proteins, the process comprising the steps of:
   (a) mixing together in a suspension tank a suspension comprising protein particles of a selected protein fraction precipitated from a solution containing proteins, a precipitation agent, and a buffer to provide the xixed suspension with a precipitation agent concentration and pH sufficient to selectively precipitate the selected protein fraction;
   (b) withdrawing a portion of the suspension from the suspension tank to thereby form a recycle stream;
   (c) mixing fresh protein solution containing proteins of the selected protein fraction directly into the recycle stream to thereby form a mixed recycle stream, whereby at least a portion of the selected protein fraction in the fresh protein solution precipitates onto previously precipitated selected protein fraction particles suspended in the mixed recycle stream;
   (d) introducing the mixed recycle stream back into the suspension tank;
   (e) withdrawing a portion of the suspension from the tank in a product stream; and
   (f) recovering from the product stream the precipitated selected protein fraction particles.

9. The process according to claim 8 wherein the precipitation agent is ethanol.

10. The process according to claim 8 comprising spraying the buffer solution and precipitation agent separately, in the form of a mist, onto the surface of the suspension in the suspension tank.

11. A continuous process for separating a selected protein fraction from a solution containing proteins comprising the steps of:
   introducing a selected amount of a precipitation agent into a suspension tank containing a suspension comprising protein particles of a selected protein fraction precipitated from a solution comprising proteins;
   mixing the precipitation agent with the suspension in the suspension tank;
   monitoring the pH and temperature of the suspension in the suspension tank;
   introducing a buffer solution into the suspension tank and mixing the buffer solution into the suspension for maintaining the pH of the suspension at a selected value;
   continuously withdrawing a portion of the suspension from the suspension tank to thereby form a recycle stream;
   continuously introducing a selected amount of fresh protein solution containing proteins of the selected protein fraction directly into the recycle stream and mixing the fresh protein solution and recycle stream together to thereby form a mixed recycle stream, the temperature of the suspension sufficient to provide the mixed recycle stream at a selected temperature so that at least a portion of the selected protein fraction contained in the fresh protein solution precipitates onto previously precipitated particles of the selected protein fraction suspended in the mixed recycle stream;

continuously introducing the mixed recycle stream back into the suspension tank;

withdrawing a portion of the suspension from the suspension tank in a product stream; and separating from the product stream the precipitated selected protein fraction and a supernatant liquid.

12. The continuous process according to claim 11 wherein the precipitation agent is sprayed onto the surface of the suspension.

13. The continuous process according to claim 12 wherein the precipitation agent is sprayed as a mist with an average particle size of less than about 100 μm.

14. The continuous process according to claim 11 wherein the precipitation agent is ethanol.

15. The continuous process according to claim 11 wherein the buffer solution is sprayed onto the surface of the suspension.

16. The continuous process according to claim 15 wherein the buffer solution is sprayed as a mist with an average particle size of less than about 100 μm.

17. A continuous multi-stage process for separation of protein fractions from blood plasma, comprising the steps of:

in a first stage:
spraying a selected amount of a precipitation agent into a suspension tank containing a suspension comprising Fraction I protein particles precipitated from blood plasma;

mixing the precipitation agent with the suspension in the suspension tank;

monitoring the pH and temperature of the suspension in the suspension tank;

spraying a buffer solution into the suspension tank and mixing the buffer solution into the suspension for maintaining the pH of the suspension at a selected value;

continuously withdrawing a portion of the suspension from the suspension tank to thereby form a recycle stream;

continuously introducing a selected amount of fresh blood plasma containing Fraction I proteins directly into the recycle stream and mixing the fresh blood plasma and recycle stream together to thereby form a mixed recycle stream, the temperature of the suspension sufficient to provide the mixed recycle stream at a selected temperature so that at least a portion of the Fraction I proteins contained in the fresh blood plasma precipitate onto previously precipitated Fraction I particles suspended in the mixed recycle stream;

continuously introducing the mixed recycle stream back into the suspension tank;

continuously withdrawing a portion of the suspension from the suspension tank in a first stage product stream;

separating from the first stage product stream the precipitated Fraction I protein particles and a supernatant liquid comprising Fraction II/III proteins;

and in a second stage:
introducing the supernatant liquid from the first stage into the recycle stream of the second stage, wherein the second stage recycle stream comprises a suspension of Fraction II/III protein particles and is at a pH, temperature, and precipitation agent concentration for selectively precipitating Fraction II/III protein particles for recovery of the Fraction II/III proteins.

18. The continuous multi-stage process of claim 17 wherein the process is repeated from stage to stage until Fraction V proteins are precipitated and recovered.

19. The continuous multi-stage process of claim 17 wherein the precipitation agent is ethanol.

20. A process for recovering a selected protein fraction from a solution containing proteins, the process comprising the steps of:

withdrawing from a suspension tank a portion of a suspension contained therein to form a recycle stream, the withdrawn suspension containing particles of a selected protein fraction precipitated from a solution containing proteins;

introducing fresh protein solution comprising proteins of the selected protein fraction directly into the recycle stream wherein the fresh protein solution is the only solution introduced directly into the recycle stream;

mixing the fresh protein solution into the recycle stream to thereby form a mixed recycle stream, whereby at least a portion of the selected protein fraction proteins in the fresh protein solution precipitate onto previously precipitated selected protein fraction particles suspended in the mixed recycle stream;

introducing the mixed recycle stream back into the suspension tank;

withdrawing a portion of the suspension from the suspension tank in a product stream; and recovering from the product stream the precipitated selected protein fraction particles.

21. The process according to claim 20 additionally comprising spraying a selected amount of buffer solution and a selected amount of precipitation agent separately onto the surface of the suspension in the suspension tank and mixing the buffer solution and precipitation agent into the suspension so that the suspension is maintained at a pH and precipitation agent concentration sufficient to selectively precipitate the selected protein fraction.

22. The process according to claim 20 wherein the precipitation agent is ethanol.

23. A process for recovering a selected protein fraction from a solution containing proteins, the process comprising the steps of:

(a) mixing together in a suspension tank a suspension comprising protein particles of a selected protein fraction precipitated from a solution containing proteins, a precipitation agent, and a buffer to provide the mixed suspension with a precipitation agent concentration and pH sufficient to selectively precipitate the selected protein fraction;

(b) withdrawing a portion of the suspension from the suspension tank to thereby form a recycle stream;

(c) introducing fresh protein solution containing proteins of the selected protein fraction directly into the recycle stream wherein the fresh protein solution is the only solution introduced directly into the recycle stream;

(d) mixing the fresh protein solution into the recycle stream to thereby form a mixed recycle stream, whereby at least a portion of the selected protein fraction in the fresh protein solution precipitates onto previously precipitated selected protein fraction particles suspended in the mixed recycle stream;

(e) introducing the mixed recycle stream back into the suspension tank;

(f) withdrawing a portion of the suspension from the tank in a product stream; and (g) recovering from the product stream the precipitated selected protein fraction particles.

24. The process according to claim 23 wherein the precipitation agent is ethanol.

25. The process according to claim 23 comprising spraying the buffer solution and precipitation agent separately, in the form of a mist, onto the surface of the suspension in the suspension tank.

26. A continuous process for separating a selected protein fraction from a solution containing proteins comprising the steps of:

spraying a selected amount of a precipitation agent onto the surface of a suspension in a suspension tank, the suspension comprising protein particles of a selected protein fraction precipitated from a solution comprising proteins;

mixing the precipitation agent with the suspension in the suspension tank;

monitoring the pH and temperature of the suspension in the suspension tank;

spraying a buffer solution onto the surface of the suspension in the suspension tank and mixing the buffer solution into the suspension for maintaining the pH of the suspension at a selected value;

continuously withdrawing a portion of the suspension from the suspension tank to thereby form a recycle stream;

continuously introducing a selected amount of fresh protein solution containing proteins of the selected protein fraction directly into the recycle stream wherein the fresh protein solution is the only solution introduced directly into the recycle stream;

mixing the fresh protein solution and recycle stream together to thereby form a mixed recycle stream, the temperature of the suspension being sufficient to provide the mixed recycle stream at a selected temperature so that at least a portion of the selected protein fraction contained in the fresh protein solution precipitates onto previously precipitated particles of the selected protein fraction suspended in the mixed recycle stream;

continuously introducing the mixed recycle stream back into the suspension tank;

withdrawing a portion of the suspension from the suspension tank in a product stream; and separating from the product stream the precipitated selected protein fraction and a supernatant liquid.

27. The continuous process according to claim 26 wherein the precipitation agent is sprayed as a mist with an average particle size of less than about 100 μm.

28. The method according to claim 26 wherein the precipitation agent is ethanol.

29. The continuous process according to claim 26 wherein the buffer solution is sprayed as a mist with an average particle size of less than about 100 μm.

30. A continuous multi-stage process for separation of protein fractions from blood plasma, comprising the steps of:

in a first stage:

spraying a selected amount of a precipitation agent into a suspension tank containing a suspension comprising Fraction I protein particles precipitated from blood plasma;

mixing the precipitation agent with the suspension in the suspension tank;

monitoring the pH and temperature of the suspension in the suspension tank;

spraying a buffer solution into the suspension tank and mixing the buffer solution into the suspension for maintaining the pH of the suspension at a selected value;

continuously withdrawing a portion of the suspension from the suspension tank to thereby form a recycle stream;

continuously introducing a selected amount of fresh blood plasma containing Fraction I proteins directly into the recycle stream wherein the fresh blood plasma is the only solution introduced directly into the recycle stream mixing the fresh blood plasma and recycle stream together to thereby form a mixed recycle stream, the temperature of the suspension sufficient to provide the mixed recycle stream at a selected temperature so that at least a portion of the Fraction I proteins contained in the fresh blood plasma precipitate onto previously precipitated Fraction I particles suspended in the mixed recycle stream;

continuously introducing the mixed recycle stream back into the suspension tank;

continuously withdrawing a portion of the suspension from the suspension tank in a first stage product stream;

separating from the first stage product stream the precipitated Fraction I protein particles and a supernatant liquid comprising Fraction II/III proteins;

and in a second stage:

introducing the supernatant liquid from the first stage directly into the recycle stream of the second stage wherein the supernatant liquid from the first stage is the only solution introduced directly into the recycle stream, the second stage recycle stream comprising a suspension of Fraction II/III protein particles and being at a pH, temperature, and precipitation agent concentration sufficient for selectively precipitating Fraction II/III protein particles for recovery of the Fraction II/III proteins.

31. The continuous multi-stage process of claim 31 wherein the process is repeated from stage to stage until Fraction V proteins are precipitated and recovered.

32. The continuous multi-stage process of claim 31 wherein the precipitation agent is ethanol.

* * * * *

UNITED STATES PATENT AND TRADEMARK OFFICE
CERTIFICATE OF CORRECTION

PATENT NO. : 4,486,341

DATED : December 4, 1984

INVENTOR(S) : Chong E. Chang

It is certified that error appears in the above-identified patent and that said Letters Patent is hereby corrected as shown below:

Column 4, line 19, "µbelieved" should be -- µm is believed --.

Column 10, line 18, "xixed" should be -- mixed --.

Column 14, line 58, "claim 31" should be -- claim 30 --.

Column 14, line 61, "claim 31" should be -- claim 30 --.

Signed and Sealed this

Thirtieth Day of July 1985

[SEAL]

Attest:

DONALD J. QUIGG

*Attesting Officer*   Acting Commissioner of Patents and Trademarks